United States Patent [19]

Ocel et al.

[11] 4,177,807

[45] Dec. 11, 1979

[54] RESTRAINING BELT FOR PATIENTS IN WHEELCHAIRS, STRETCHERS OR THE LIKE

[75] Inventors: John J. Ocel; Thomas Ocel; Donald J. Ocel, all of Minneapolis, Minn.

[73] Assignee: Ocelco, Inc., Minneapolis, Minn.

[21] Appl. No.: 902,832

[22] Filed: May 4, 1978

[51] Int. Cl.² ............................................. A61F 13/00
[52] U.S. Cl. .................................... 128/133; 24/223; 297/482
[58] Field of Search .............................. 128/132–135, 128/DIG. 15; 297/385; 24/223; 5/92, 336

[56] References Cited

U.S. PATENT DOCUMENTS

| | | | |
|---|---|---|---|
| 2,543,933 | 3/1951 | Pommier | 24/223 |
| 3,191,599 | 6/1965 | Kendell | 5/92 |
| 3,318,634 | 5/1967 | Nicholas | 297/385 |
| 3,397,913 | 8/1968 | Fein | 297/385 |
| 3,485,529 | 12/1969 | Marling | 297/385 |
| 3,535,719 | 10/1970 | Murcott | 128/133 |
| 4,108,170 | 8/1978 | Spann | 128/134 |
| 4,125,920 | 11/1978 | Grimes | 24/223 |

*Primary Examiner*—Lawrence W. Trapp

*Attorney, Agent, or Firm*—Orrin M. Haugen; Thomas J. Nikolai

[57] ABSTRACT

A restraining belt for securing a patient to a wheelchair, stretcher, bed or similar implement and for inhibiting the accidental uncoupling thereof or the intentional uncoupling by a patient being restrained. The belt comprises a flexible strap of a desired length which is adapted to be passed around the body of the patient and around the implement to which the patient is being secured and has the cooperating parts of a Velcro-type hook and loop fastener elements disposed on opposed surfaces thereof and extending a predetermined distance from the ends of the belt towards its center, such that when the ends are overlapped, the Velcro hook pad abuts the Velcro loop pad. Further included is a flexible, fabric sleeve, having a length generally the same as that of the Velcro pads. The sleeve is attached to one end of the strap at a point intermediate the two ends thereof and can be drawn back or collapsed so as to expose the Velcro pad on one of the ends. After the two ends are overlapped and thereby coupled, the flexible sleeve may be extended to substantially enclose the entire area of the Velcro fastener.

3 Claims, 4 Drawing Figures

RESTRAINING BELT FOR PATIENTS IN WHEELCHAIRS, STRETCHERS OR THE LIKE

BACKGROUND OF THE INVENTION

I. Field of the Invention

This invention relates generally to restraining belts for use with medical appliances, and more specifically to an improved restraining belt which is relatively easy for the attendant to secure, but which is relatively difficult for the patient to uncouple when properly positioned with respect to the implement with which the restraining belt is being utilized.

II. Description of the Prior Art

It is known in the art to utilize a restraining belt for securing a patient into a wheelchair or on a stretcher. Also, Velcro-type fasteners have been employed in the prior art to secure the two ends of the belt together. For example, reference is made to the Posey U.S. Pat. No. 3,669,107 which illustrates a variety of restraining straps attached to a wheelchair or the like, and used to secure or otherwise restrain a patient. Reference is similarly made to the Ochs U.S. Pat. No. 3,889,668, the Kroeger U.S. Pat. No. 3,817,245 and the Huggins U.S. Pat. No. 3,729,752 for related apparatus.

In some applications, it is desired that a restraining belt be used not only for securing a patient to prevent injury due to accidents, much like a automobile seatbelt or the like, but also to restrain the patient from uncoupling the belt and thereby releasing himself from the restraint.

In accordance with the teachings of the present invention, there is provided a restraining belt which includes a collapsible sleeve which may be extended over the Velcro joint between the overlapping ends of the belt so that when the sleeve is in its extended position, the patient is unable to, himself, uncouple the belt. The restraining belt of the present invention comprises a flexible strap having a desired length which permits it to be looped around the body of a patient and around an implement to which the patient is to be secured. Opposed surfaces of the belt have attached at the end portions thereof the cooperating parts of a Velcro-type fastener and arranged such that when the two ends are overlapped, these cooperating parts mate to effect a coupling or fastening. There is also provided a flexible fabric sleeve which is attached at one end thereof to the restraining belt at a point intermediate the end portions of the belt. Being made from fabric, the sleeve may be manually collapsed by sliding the sleeve towards its point of connection with the belt to thereby expose the Velcro pad area on its end portion. When the two ends are then brought together and coupled, the fabric sleeve may be extended to substantially cover the Velcro fastener and this cover inhibits the ability of a patient to uncouple the two ends of the restraining belt. When used with a wheelchair, one end of the belt is fixedly attached to the back frame members of the chair and the restraining belt is of a length which will pass around the torso of the patient to the rear of the seat back where the coupling is effected. When the fabric sleeve is extended to cover the mating ends of the restraining belt, it becomes difficult, if not impossible, for the patient to reach around to the back of the chair, withdraw the sleeve and unfasten the Velcro coupling.

OBJECTS

It is accordingly the principal object of the present invention to provide a new and improved restraining belt for use with invalids and the like.

Another object of the invention is to provide a restraining belt which utilizes Velcro-type coupling elements and which includes a means for inhibiting the accidental or intentional uncoupling of the belt by the patient.

Still another object of the invention is to provide a restraining belt having Velcro fastening pads on each end thereof and which further includes a fabric sleeve secured at one of its ends to the belt at a point intermediate the two ends thereof and which may be drawn back toward the point of connection to expose the Velcro pad on one end of the belt so that it may be joined with the cooperating pad on the opposite end of the belt and which can then be extended to substantially cover the entire area of the overlapping ends.

These and other objects and advantages of the invention will become apparent to those of ordinary skill in the art from the following detailed description of the preferred embodiment, when considered in conjunction with the accompanying drawings in which like numerals in the several view identify corresponding parts.

DESCRIPTION OF THE PREFERRED EMBODIMENT

Figure 1:
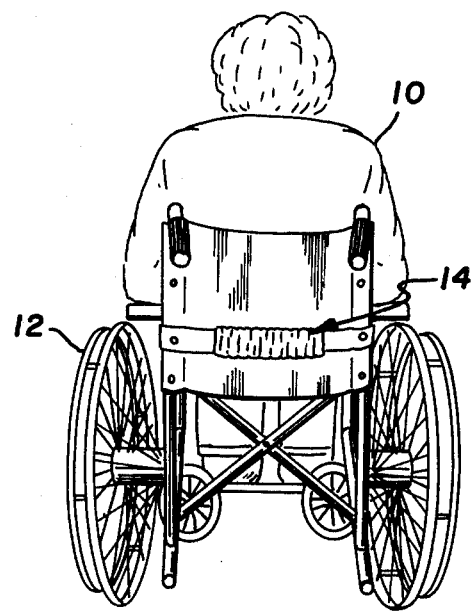
FIG. 1 is a rear view showing a patient seated in a wheelchair and incorporating the restraining belt of the present invention.
Figure 2:
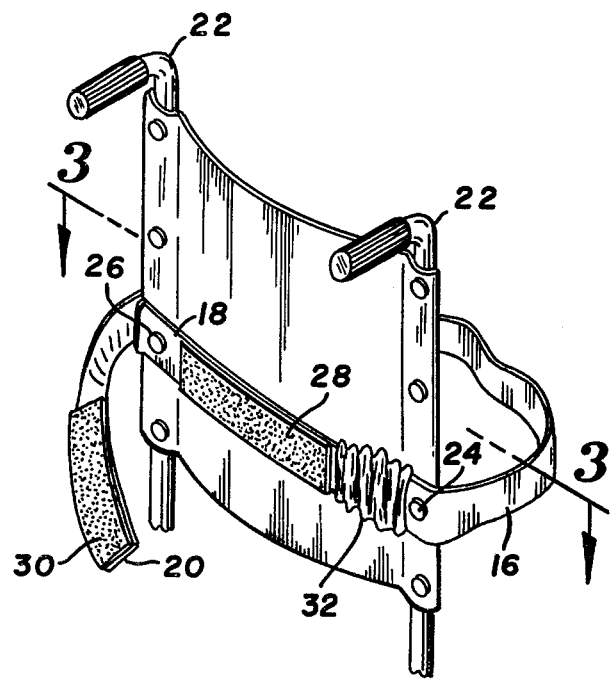
FIG. 2 is an enlarged perspective view showing the restraining belt in conjunction with a wheelchair frame.

Referring to FIG. 1, there is shown a patient 10 sitting in a conventional wheelchair 12. Holding the patient in the wheelchair is the restraining belt of the present invention, which is indicated generally by the numeral 14. As can best be seen in FIG. 2, the restraining belt comprises an elongated flexible strap 16 having a first end portion 18 and a second end portion 20. The first end portion 18 is fixedly attached to the back frame members 22–22 of the wheelchair by means of screws 24 and 26. Sewn or otherwise attached to the outer surface of the flexible belt 16 in the neighborhood of the first end thereof 18 is a Velcro-type pad 28.

As is well-known in the art, a Velcro-type fastener includes first and second pads, one being of a material having a large multiplicity of fabric loops extending therefrom while the other mating pad of the Velcro fastener comprises a flexible backing having a large multiplicity of hook members projecting therefrom. When the hook-pad is abutted against the loop-pad, the hooks engage the loops to provide a rather secure connection which can be separated by a rather modest force in a direction perpendicular to the plane of intersection, but which can withstand rather large tensile forces applied in a direction parallel to the plane of intersection without separating.

The mating Velcro pad 30 is sewn or otherwise affixed to the end portion 20 of the belt 16 and extends for a predetermined distance inwardly along the surface of the strap 16 from its end point.

Identified by the numeral 32 is a collapsible sleeve 32 which is preferably formed from a suitable fabric. The screw 24 is arranged to pass through the strap 16 and through the inner side of the sleeve 32 and into the wheelchair frame 22. Thus, one end of the collapsible sleeve 32 is affixed to the wheelchair frame.

Figure 3:
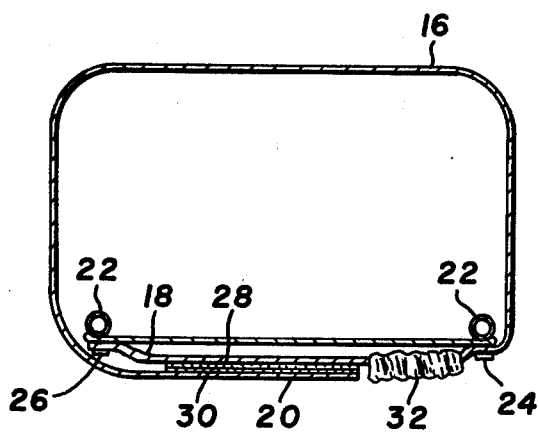
FIG. 3 is a cross-sectional view taken along the lines 3—3 in FIG. 2.

FIG. 3 is a top cross-sectional view showing the two ends of the strap 16 overlapped with their mating Velcro pads in engagement with one another and with the sleeve 32 shown in its collapsed orientation.

Figure 4:
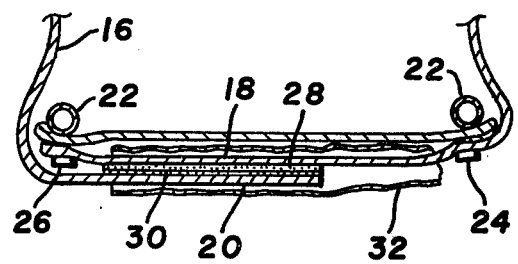
FIG. 4 is a partial cross-sectional view showing the sleeve member in its extended position.

FIG. 4 shows a similar view, only with the sleeve 32 shown in its extended orientation to substantially enclose the mating ends 18 and 20 of the strap 16. When the ends are so covered, it becomes practically impossible for a confined patient to reach around behind the back of the chair 12, manipulate the sleeve member 32 to its collapsed condition and then apply a normal, separating force to the Velcro fastening elements. However, it is extremely simple for a nurse or other attendant to draw back the collapsible fabric sleeve 32 to expose the overlapping ends of the restraining belt 16 and apply the separating force in the direction normal to the connecting surfaces of the Velcro fastener.

When the present invention is utilized with a stretcher or bed, it is only necessary that the junction between the opposing ends of the strap 16 be located in a difficult-to-reach location as far as the patient is concerned.

Since various modifications and changes to the preferred embodiment may occur to persons of ordinary skill after having had the benefit of the teachings of the instant specification, the scope of the invention should be determined strictly from the accompanying claims.

What is claimed is:

1. A restraining strap for securing a patient to a patient-transporting device, comprising:
   (a) a unitary, woven, flexible strap having first and second end portions of predetermined lengths;
   (b) Velcro-type fastening means attached to the inner and outer surfaces of said strap along said first and second end portions, respectively; and
   (c) a collapsible, tubular fabric sleeve surrounding said first end portion of said strap and having one end thereof attached to said strap at a point intermediate said first and second end portions and extending a predetermined distance toward the terminus of said first end portion.

2. Apparatus as in claim 1 wherein said collapsible sleeve, when extended, surrounds substantially the entire lengths of both said first and second end portions of said strap when said inner and outer surfaces of said end portions are overlapped and, when collapsed, exposes said overlapped first and second end portions.

3. The apparatus as in claim 1 and further including means for attaching said first end portion of said strap to said patient transporting device at plural spaced-apart points along said predetermined length.

* * * * *